US012599487B2

(12) United States Patent　　　(10) Patent No.:　US 12,599,487 B2
Glazer et al.　　　　　　　　　　　(45) Date of Patent:　　　Apr. 14, 2026

(54) TOOLS AND IMPLANTS FOR LATERAL DISC REPLACEMENT

(71) Applicant: SG, LLC, Boston, MA (US)

(72) Inventors: Paul Glazer, Boston, MA (US);
Michael J. Milella, Jr., Escondido, CA (US)

(73) Assignee: SG, LLC, Highland Beach, FL (US)

( * ) Notice: Subject to any disclaimer, the term of this patent is extended or adjusted under 35 U.S.C. 154(b) by 213 days.

(21) Appl. No.: 18/221,849

(22) Filed: Jul. 13, 2023

(65) Prior Publication Data

US 2025/0017741 A1　　Jan. 16, 2025

(51) Int. Cl.
*A61F 2/44*　　　　(2006.01)

(52) U.S. Cl.
CPC ...... *A61F 2/4425* (2013.01); *A61F 2002/443* (2013.01); *A61F 2310/00005* (2013.01); *A61F 2310/00011* (2013.01)

(58) Field of Classification Search
CPC .............. A61F 2/4425; A61F 2002/443; A61F 2002/4435; A61F 2002/4445
See application file for complete search history.

(56) References Cited

U.S. PATENT DOCUMENTS 8,147,552 B2　4/2012　Ralph et al.
8,353,964 B2 *　1/2013　Carpenter ............. A61F 2/4611
　　　　　　　　　　　　　　　　623/17.16

8,728,166 B2　5/2014　Schwab
8,795,372 B2　8/2014　Christensen
9,039,773 B2　5/2015　Mather et al.
9,504,584 B1　11/2016　Stein et al.
9,610,171 B2　4/2017　Curran et al.
9,883,945 B2　2/2018　de Villiers et al.
10,779,956 B2　9/2020　Perrow
10,869,767 B2　12/2020　Mermuys et al.
10,993,813 B2　5/2021　Balasubramanian et al.
11,197,766 B1 *　12/2021　Suddaby ............... A61F 2/4601
11,207,190 B2　12/2021　Arramon et al.
2003/0045939 A1 *　3/2003　Casutt ..................... A61F 2/442
　　　　　　　　　　　　　　　　623/17.15
2004/0243238 A1 *　12/2004　Arnin .................... A61F 2/4425
　　　　　　　　　　　　　　　　623/17.13

(Continued)

FOREIGN PATENT DOCUMENTS

EP　　　2386274 B1　　1/2018
JP　　　5395054 B2　　1/2014

(Continued)

*Primary Examiner* — Matthew J Lawson
(74) *Attorney, Agent, or Firm* — Troutman Pepper Locke LLP; Joshua L. Jones; Gabrielle L. Gelozin

(57)　　　　　　ABSTRACT

In accordance with at least one aspect of this disclosure, a disc replacement implant includes, a first endplate configured to engage a vertebral endplate of a first vertebra adjacent an intervertebral space, a second endplate configured to engage a vertebral endplate of a second vertebra opposite the first end plate in the intervertebral space, a core between the first and second endplates, and an annulus surrounding the core and connecting a perimeter of the first endplate to a perimeter of the second end plate. In embodiments, the annulus can include a portion that extends inwardly between the first and second core plates to the spacer.

15 Claims, 7 Drawing Sheets

(56)          References Cited

U.S. PATENT DOCUMENTS

| | | | | |
|---|---|---|---|---|
| 2005/0027364 A1* | 2/2005 | Kim | ..................... | A61F 2/4425 623/17.13 |
| 2006/0293752 A1* | 12/2006 | Moumene | ............. | A61F 2/4425 623/17.13 |
| 2007/0270952 A1* | 11/2007 | Wistrom | ............... | A61F 2/4611 623/17.11 |
| 2011/0082552 A1* | 4/2011 | Wistrom | ............... | A61F 2/4425 623/17.16 |
| 2013/0158665 A1* | 6/2013 | Josse | .................... | A61F 2/4425 623/17.16 |
| 2017/0258604 A1 | 9/2017 | Barrett et al. | | |
| 2019/0021869 A1 | 1/2019 | Paul et al. | | |
| 2019/0167441 A1* | 6/2019 | Suddaby | ................. | A61F 2/447 |
| 2021/0298914 A1* | 9/2021 | Krämer | .................. | A61F 2/442 |

FOREIGN PATENT DOCUMENTS

| | | | |
|---|---|---|---|
| JP | 2022024022 | A | 2/2022 |
| WO | 200428415 | A1 | 4/2004 |

* cited by examiner

TOOLS AND IMPLANTS FOR LATERAL DISC REPLACEMENT

BACKGROUND

1. Field

The present disclosure relates to orthopedic surgery, and more particularly to intervertebral disc replacement.

2. Description of Related Art

Various conditions and circumstances can cause degeneration and dysfunction of intervertebral discs. Certain of these conditions can be treated by removing the tissue of the disc and replacing the disc with a prosthetic disc to maintain the space between the vertebrae adjacent the removed disc. Some prosthesis facilitate a fusion of the two adjacent vertebrae wherein the loss of relative motion between the two vertebrae is an acceptable outcome. Other disc replacement prostheses may allow for some relative motion of the two affected vertebrae to preserve mobility of the patient.

Generally the discectomy and implanting of the disc replacement are performed through an anterior approach or ALIF (anterior lumbar interbody fusion). This approach allows direct access to the disc and intervertebral space, avoiding the dorsal structures of the spine. However, in order to start the discectomy in a lumbar region, the anterior approach involves creating and maintaining a clear opening through the abdomen, from the front of the patent to the spine, with special care to avoiding the major blood vessels of the lumbar and pelvic region. In practical terms, just creating the path for performing the discectomy in an anterior approach can be a fairly involved open surgery on its own before even beginning the discectomy.

Other approaches have been used such as the transforaminal approach (for transforaminal lumbar interbody fusion or TLIF) and the lateral approach, sometimes called LLIF (lateral lumbar interbody fusion) or XLIF (extreme lateral interbody fusion). For the lateral approach, a smaller surgical opening can be created through a patient's side. This can involve splitting an opening through the Psoas muscle in the case of a lumbar disc replacement, for example, but simplifies access to the disc and intervertebral space considerably enough to be considered minimally invasive.

One factor keeping surgeons from using the lateral approach is that most disc replacement implants are designed for the anterior approach. Many of these may not fit through the minimally invasive opening of an anterior approach. Moreover, the delivery tools designed for traditional disc replacement implants tend not to be conducive to delivery through the lateral approach.

The conventional techniques have been considered satisfactory for their intended purpose. However, there is an ever present need for improved systems and methods for tools and implants for lateral disc replacement. This disclosure provides a solution for this need.

SUMMARY

In accordance with at least one aspect of this disclosure, a disc replacement implant includes, a first endplate configured to engage a vertebral endplate of a first vertebra adjacent an intervertebral space, a second endplate configured to engage a vertebral endplate of a second vertebra opposite the first end plate in the intervertebral space, a core between the first and second endplates, and an annulus surrounding the core and connecting a perimeter of the first endplate to a perimeter of the second end plate. In embodiments, the annulus can include a portion that extends inwardly between the first and second core plates to the spacer.

In embodiments, the first endplate and second end plate can be metallic. In embodiments, the core can be of a material more flexible than that of the first and second endplates. In certain embodiments, the core can be of a polymer material. For example, in certain embodiments, the core can be of poly-ether-ether-ketone (PEEK). In embodiments, the core can be machined, injection, molded and/or 3D printed. In certain embodiments, the annulus can be of a material more flexible than that of the core. In embodiments, a flexibility of the annulus and the core can be configured to provide a combination of elasticity that simulates a real disc. In certain embodiments, the annulus can be overmolded onto the assembly of the endplates and core. In certain embodiments, the annulus can be of viscoelastic material. For example, in certain embodiments, the annulus can be of thermoplastic polyurethane (TPU) or Bionate®.

In embodiments, the core can include a first core plate that engages an inner surface of the first endplate, a second core plate that engages an inner surface of the second endplate, and a spacer between the first and second core plates. In embodiments, the spacer can be connected to each of the first and second core plates and can be configured to allow bending and twisting motion of the first and second core plates relative to one another. In certain embodiments, the spacer can include a spherical section, which can provide a centroid of motion for the two core plates in bending and twisting, configured to connect a center portion of the first core plate to a center portion of the second core plate. The spacer can have a neutral position that maintains a wedge angle and spacing between the first and second core plates. In embodiments, the spacer structure can be configured to provide the implant flexion capability in the sagittal and coronal planes, and provides axial twisting. In certain embodiments, one or more ribs radiate from the spacer toward lateral edges of the core plates (e.g., to provide stiffness across the core plates).

In embodiments, a first pocket can be defined between the first endplate and the first core plate and defined as a recess in the outward face of the first core plate, and/or the inward surface of the first endplate. A second pocket can be defined between the second endplate and the second core plate and defined as a recess in the outward face of the second core plate, and/or the inward surface of the second endplate. In embodiments, a plurality of holes can be defined through the first end plate from an external surface of the first endplate into the first pocket for osseointegration, and a plurality of holes can be defined through the second endplate from an external surface of the second endplate into the second pocket for osseointegration.

In embodiments, the first endplate can have an external surface defining a plurality of pyramidal teeth, and the second endplate can have an external surface defining a plurality of pyramidal teeth. In certain embodiments, a plurality of the pyramidal teeth of the first endplate can include osseointegration holes defined through each pyramidal face thereof. In certain embodiments, the plurality of the pyramidal teeth of the second endplate can have osseointegration holes defined through each pyramidal face thereof. In certain embodiments, one or more of the osseointegration holes can communicate into the first and/or second pocket. In certain embodiments, one or more of the osseointegration holes can be blind pockets, such that the blind holes allow for osseointegration, but not for communication into the first and/or second pocket. In certain embodiments one or more of the pyramidal teeth can have no osseointegration holes defined therethrough.

The first endplate can have a biologics aperture therethrough from the external surface of the first endplate into the pocket. In embodiments, the biologics aperture can be larger in diameter than the osseointegration holes, for introduction of osseointegration biologics into the first pocket. In embodiments, the second endplate can a biologics aperture therethrough similar to the first endplate for introduction of osseointegration biologics into the second pocket.

In embodiments, an inserter pocket can be defined on a first end of the first endplate, second endplate, and the annulus. In embodiments, the inserter pocket can include a first recess defined on an inward facing surface of the first end plate and a second recess defined on an inward facing surface of the second end plate. In embodiments, the second endplate can include a similar inserter pocket(s) so the implant can be implanted from either lateral side of a spinal column.

In embodiments, the inserter pocket can be defined on a first lateral end of the first endplate, the second endplate, and the annulus. The first endplate, second end plate, and annulus can have a length from the first lateral end to an opposite second lateral end of the implant thereof that is greater than a width measured from a front side of the first and second endplates and annulus to a back side thereof to facilitate implantation through a lateral approach.

In accordance with at least one aspect of this disclosure, a disc replacement tool can include a main shaft defining a proximal end and an opposed distal end, an inserter head extending from the distal end of the main shaft, an actuating knob at the proximal end of the main shaft, a rotation shaft extending from the knob through the main shaft to the inserter head, and a set of male threads in the inserter head operatively connected to be rotated around a thread axis of the threads by the rotation shaft for releasing a disc replacement implant from the inserter head.

In embodiments, the inserter head can be angled relative to the main shaft, and the set of male threads can connect to the rotation shaft through a universal joint connecting between the main shaft and the inserter head. A compression plate can be threaded on the set of male threads, and the compression plate can have a length in a first direction that is greater than a width in a second direction perpendicular to the first direction for engaging recesses in an inserter pocket of a disc replacement implant. In embodiments, a bearing can be operatively connected to the distal end of the main shaft for facilitating rotation of the shaft during rotation of the actuating knob and compression plate.

A handle can extend obliquely from a proximal portion of the main shaft, and the handle is configured to rotate about a main axis of the main shaft to reposition the handle relative to the inserter head, for example depending on which side of a patient the operation is taking place. Embodiments can include a detent in the main shaft that the handle can lock into to prevent rotation, and can be included on both sides of the main shaft for operating on either side of a patient, e.g., left or right.

In accordance with at least one aspect of this disclosure, a kit for disc replacement can include, a sterile pack, a plurality of disc implants as described above of a variety of sizes inside the sterile pack, and optionally a tool as described above.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
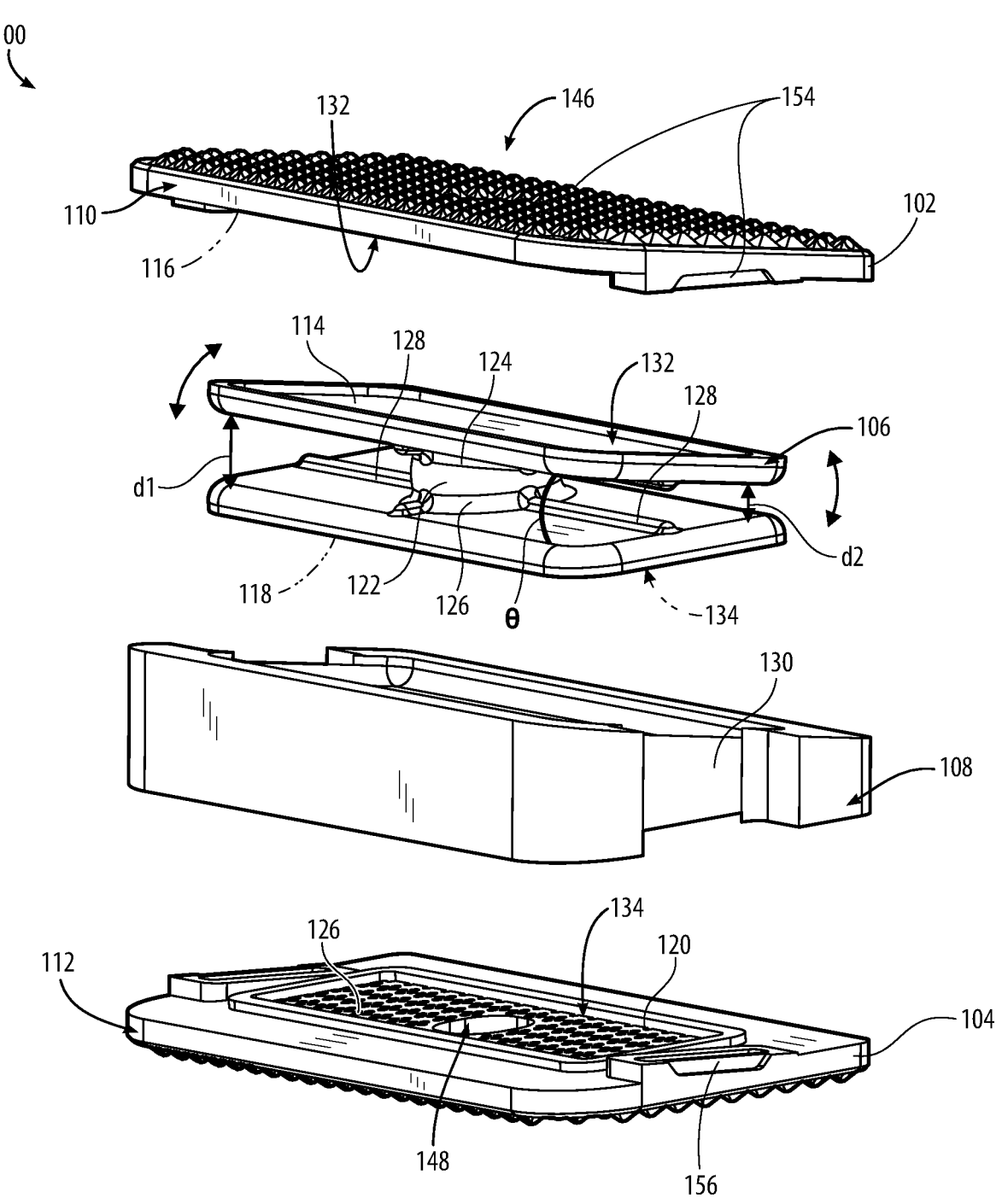
FIG. 1 is an exploded perspective view of an embodiment of an implant constructed in accordance with the present disclosure, showing the core, annulus, and endplates.

Reference will now be made to the drawings wherein like reference numerals identify similar structural features or aspects of the subject disclosure. For purposes of explanation and illustration, and not limitation, a partial view of an embodiment of a disc replacement implant in accordance with the disclosure is shown in FIG. 1 and is designated generally by reference character 100. Other embodiments of systems in accordance with the disclosure, or aspects thereof, are provided in FIGS. 2-14, as will be described.

The present disclosure relates to lateral disc replacements, including a replacement disc (e.g., implant 100 as described below), and tools for inserting the implant (e.g., tool 200 as described below). Generally, to perform an XLIF disc replacement, a small incision is made in a lower back portion of a patient 10. The Psoas muscle 12, and surrounding organs and/or tissues are moved to allow insertion of a surgical tool to remove the existing injured disc (or a portion thereof). The injured disc (or a portion thereof) is then replaced with an implant, (e.g., implant 100), using a disc replacement tool (e.g., tool 200), where the implant is configured to be inserted between vertebra 14 and 16, and configured to interface with a first side 18 of a first vertebra 14 and second side 20 of a second vertebra 16. This can be seen in FIG. 8A, where the Psoas muscle 12 is shown schematically in phantom and surrounding organs/tissues are omitted for clarity.

Figure 2:
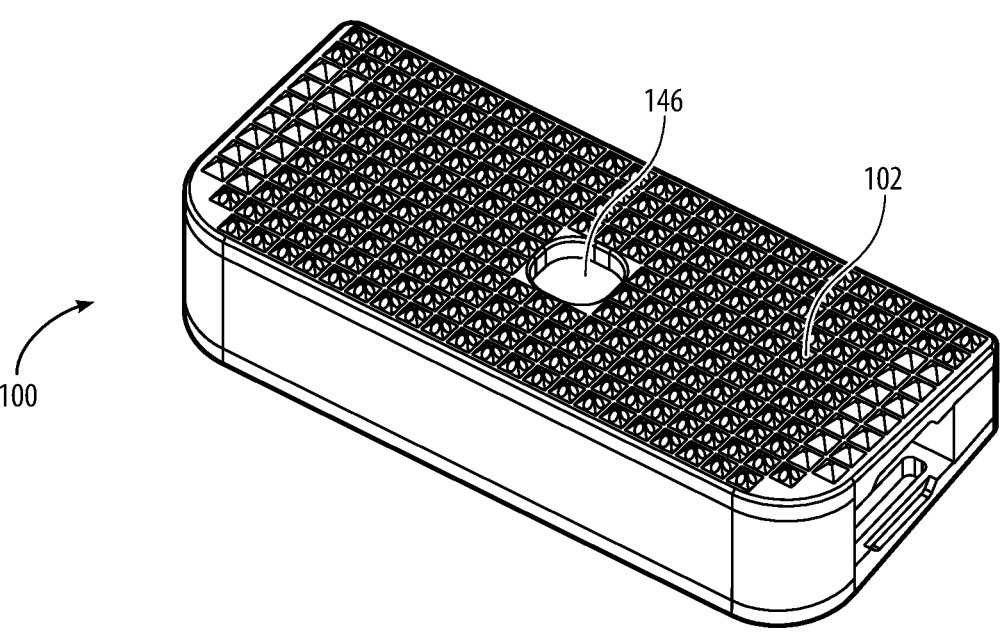
FIG. 2 is a perspective view of the implant of FIG. 1, showing the core, annulus, and endplates assembled together.
Figure 8:
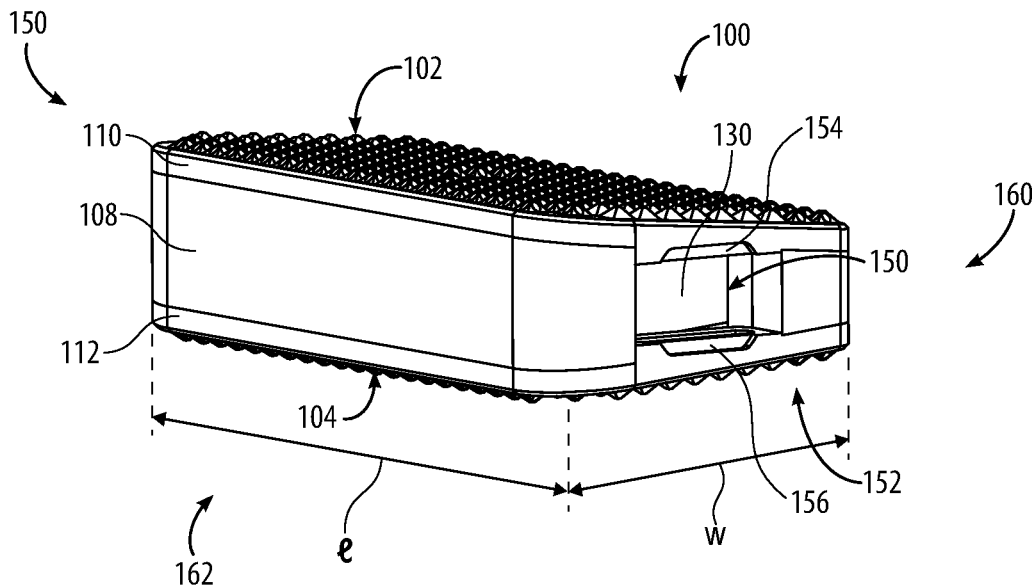
FIG. 8 is a perspective view of the implant of FIGS. 1 and 2, showing one of the implantation pockets.
Figure 8A:
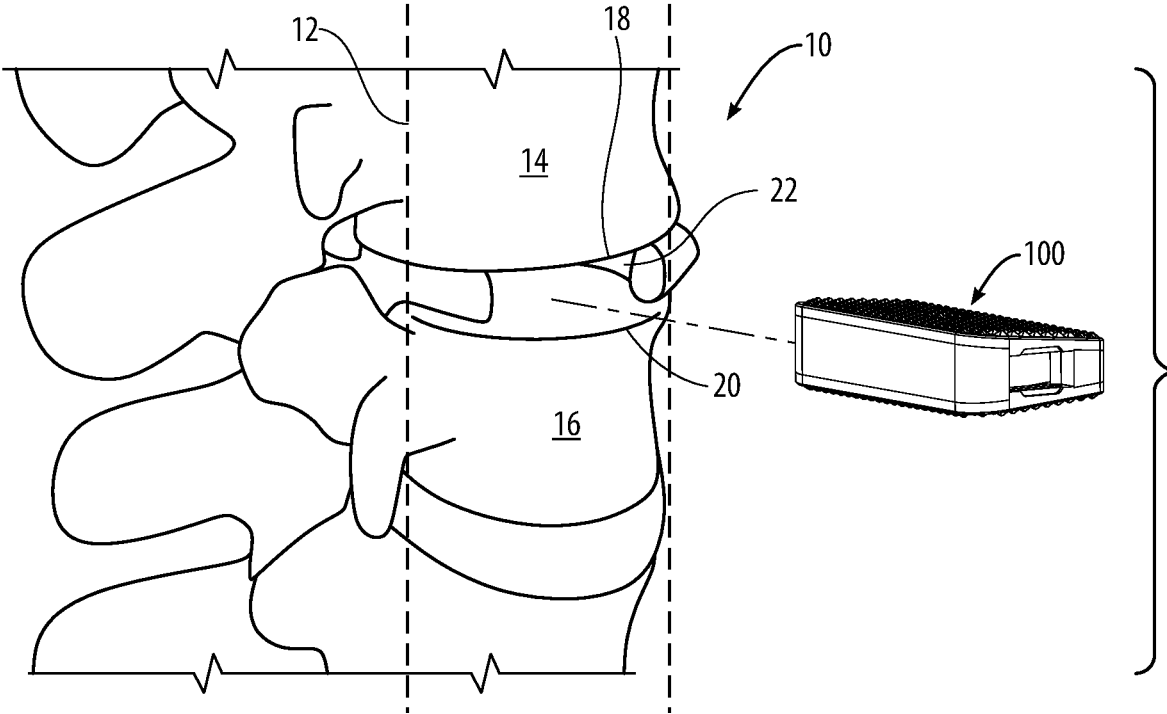
FIG. 8A is a perspective view of the implant of FIGS. 1 and 2, showing a relative location of insertion of the implant into a spine.

As shown in FIGS. 1 and 2, in accordance with at least one aspect of this disclosure, a disc replacement implant 100 includes a first endplate 102 configured to engage a vertebral endplate 18 of a first vertebra 14 adjacent an intervertebral space 22, a second endplate 104 configured to engage a vertebral endplate 20 of a second vertebra 16 opposite the first end plate 102 in the intervertebral space 22 (e.g., as shown in FIG. 8A). A core 106 is included between the first and second endplates 102, 104, and an annulus 108 can be included, surrounding the core 106 and connecting a perimeter 110 of the first endplate 102 to a perimeter 112 of the second end plate 104.

In embodiments, the first endplate 102 and second end plate 104 can be metallic. In embodiments, the core 106 can be of a material more flexible than that of the first and second endplates 102, 104. In certain embodiments, the core 106 can be of a polymer material. For example, in certain embodiments, the core 106 can be of poly-ether-ether-ketone (PEEK). In embodiments, the one or more portions of the core 106 can be machined, injection molded, and/or 3D printed. In certain embodiments, the annulus 108 can be of a material more flexible than that of the core 106. In embodiments, a flexibility of the annulus 108 and the core 106 can be configured to provide a combination of elasticity that simulates a real, natural spinal disc. In certain embodiments, the annulus 108 can be overmolded onto the assembly of the endplates 102, 104 and core 106. In certain embodiments, the annulus 108 can be of viscoelastic material. For example, in certain embodiments, the annulus 108 can be of thermoplastic polyurethane (TPU) or Bionate®. Bionate is a registered trademark of DSM Biomedical, located at 735 Pennsylvania Drive Exton, PA 19341.

Figure 3:
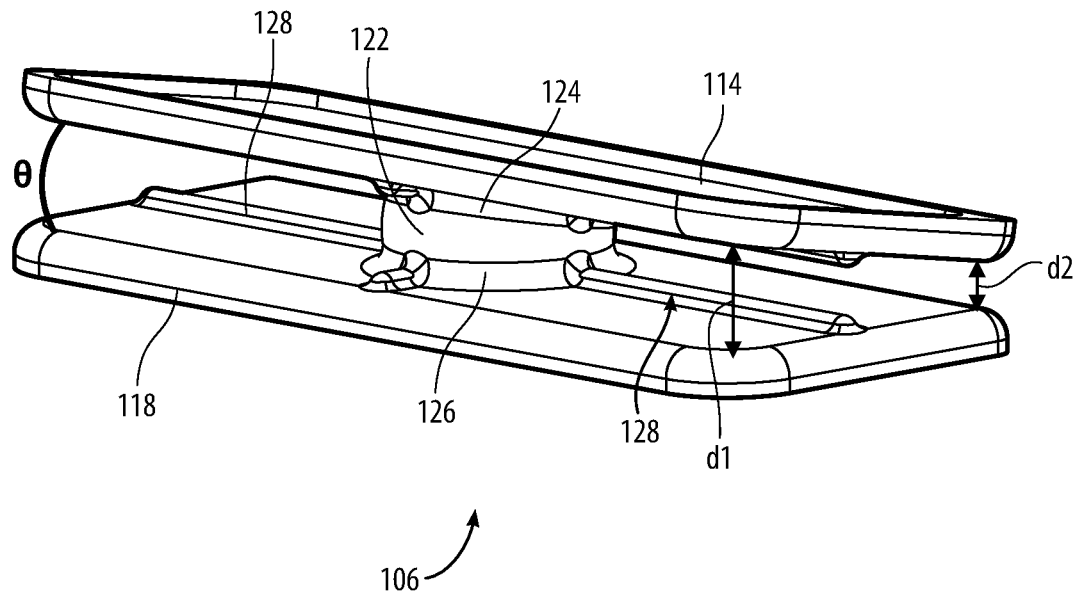
FIG. 3 is a perspective view of the core of FIG. 1, showing the core plates, flexible spacer, ribs, and pockets.

With reference to FIGS. 1 and 3, in embodiments, the core 106 can include a first core plate 114 that engages an inner surface 116 of the first endplate 102, a second core plate 118 that engages an inner surface 120 of the second endplate 104. A spacer 122 can be included between the first and second core plates 114, 118. In embodiments, the spacer 122 can be connected to each of the first and second core plates 114, 118 and can be configured to allow bending and twisting motion of the first and second core plates 114, 118 relative to one another. In certain embodiments, the spacer 122 can include a spherical section (e.g., as shown), configured to connect a center portion 124 of the first core plate 114 to a center portion 126 of the second core plate 118, which can provide a centroid of motion for the two core plates 114, 118 in bending and twisting. The spacer 122 can have a neutral position that maintains a wedge angle θ and spacing d1, d2 between the first and second core plates 114, 118. The neutral position is shown in FIG. 1. In embodiments, the spacer structure can be configured to provide the implant flexion capability in the sagittal and coronal planes, and provides axial twisting. In certain embodiments, one or more ribs 128 radiate from the spacer toward lateral edges of the core plates 114, 118 (e.g., to provide stiffness across the core plates 114, 118). In embodiments, the annulus 108 can include a portion 130 that extends inwardly between the first and second core plates 114, 118 to the spacer 122.

Figure 4:
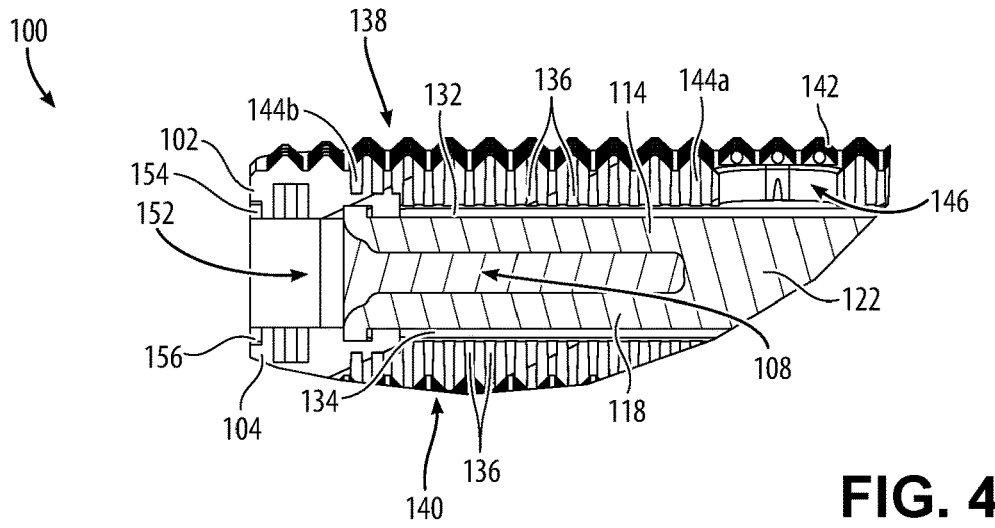
FIG. 4 is a cross-sectional perspective view of the implant of FIG. 2, showing the osseointegration pockets.
Figure 5:
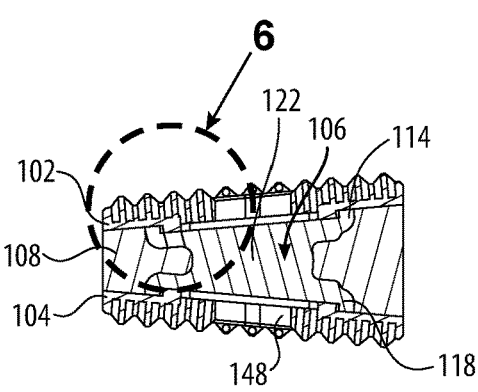
FIGS. 5-6 are cross-sectional side elevation views of the implant of FIG. 4, showing the end plates' blind holes and through holes into the pocket.
Figure 6:
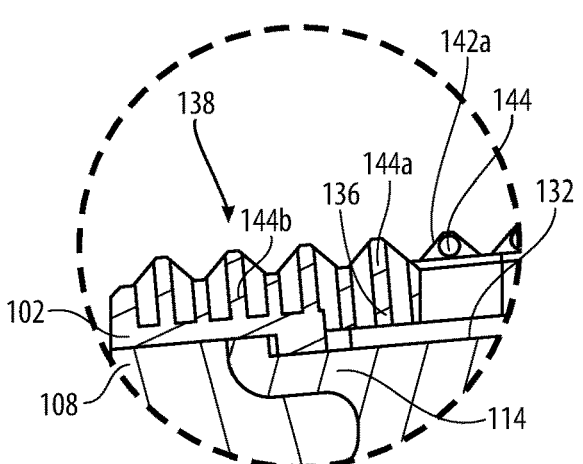
Figure 7:
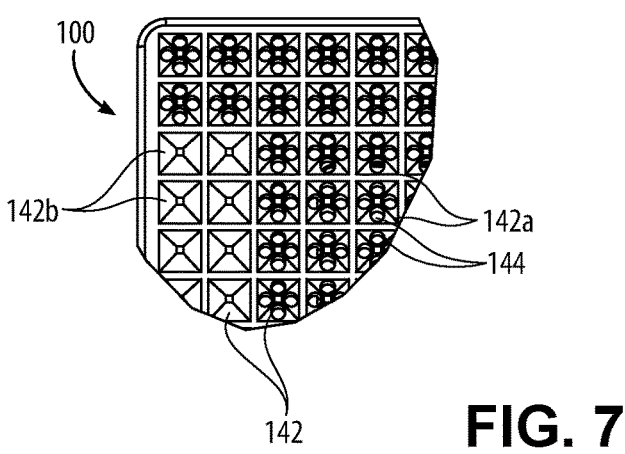
FIG. 7 is a plan view of a portion of the implant of FIG. 2, showing the pyramidal teeth, some of which include osseointegration holes in the faces thereof.

Referring now to FIGS. 1 and 4, in embodiments, a first pocket 132 can be defined between the first endplate 102 and the first core plate 114 and defined as a recess 132 in the outward face of the first core plate 114, and/or the inward surface of the first endplate 114. A second pocket 134 can be defined between the second endplate 104 and the second core plate 118 and defined as a recess 134 in the outward face of the second core plate 118, and/or the inward surface of the second endplate 104. In embodiments, a plurality of holes 136 can be defined through the first end plate 102 from an external surface 138 of the first endplate 102 into the first pocket 132 for osseointegration, and a plurality of holes 136 can be defined through the second endplate 132 from an external surface 140 of the second endplate 104 into the second pocket 134 for osseointegration.

With reference to FIGS. 4-7, each of the external surface 138 of the first end plate 102, and the external surface 140 of the second endplate 104 can define a plurality of pyramidal teeth 142. In certain embodiments, a plurality 142a of the pyramidal teeth 142 can include osseointegration holes 144 defined through each pyramidal face thereof. In certain embodiments, one or more of the osseointegration holes 144a can communicate into the first and/or second pocket 132, 134. In certain embodiments, one or more of the osseointegration holes 144b can be blind pockets, such that the blind holes 144b allow for osseointegration, but not for communication into the first and/or second pocket 132, 134. In certain embodiments one or more of the pyramidal teeth 142b can have no osseointegration holes defined therethrough.

The first endplate 102 can have a biologics aperture 146 therethrough from the external surface 138 of the first endplate into the pocket 132. In embodiments, the biologics aperture 146 can be larger in diameter than the osseointegration holes 144, for introduction of osseointegration biologics into the first pocket 132. In embodiments, the second endplate 104 can a biologics aperture 148 therethrough similar to the first endplate for introduction of osseointegration biologics into the second pocket 134.

With reference now to FIG. 8, an embodiments, an inserter pocket 150 can be defined on a first end 152 of the first endplate 102, second endplate 104, and the annulus 108. In embodiments, the inserter pocket 150 can include a first recess 154 defined on an inward facing surface of the first end plate 102 and a second recess 156 defined on an inward facing surface of the second end plate 104. In embodiments, a second end 158 can include a similar inserter pocket(s) 152 so the implant 100 can be implanted from either lateral side of a spinal column. In embodiments, the first endplate 102, second end plate 104, and annulus 108 can have a length l from the first lateral end 152 to an opposite second lateral end 158 of the implant 100 thereof that is greater than a width w measured from a front side 160 of the first and second endplates 102, 104 and annulus 108 to a back side 162 thereof to facilitate implantation through a lateral approach.

Referring now to FIGS. 9-13, in accordance with at least one aspect of this disclosure, a disc replacement tool 200 can include a main shaft 264 defining a proximal end 266 and an opposed distal end 268. The tool can also include an inserter head 270 extending from the distal end 268 of the main shaft 264, an actuating knob 272 at the proximal end 266 of the main shaft 264, a rotation shaft 274 extending from the knob 272 through the main shaft 264 to the inserter head 270, and a set of male threads 276 in the inserter head 270 operatively connected to be rotated around a thread axis of the threads 276 by the rotation shaft 274 for releasing a disc replacement implant (e.g., implant 100) from the inserter head 270.

Figures 9, 10, 11:
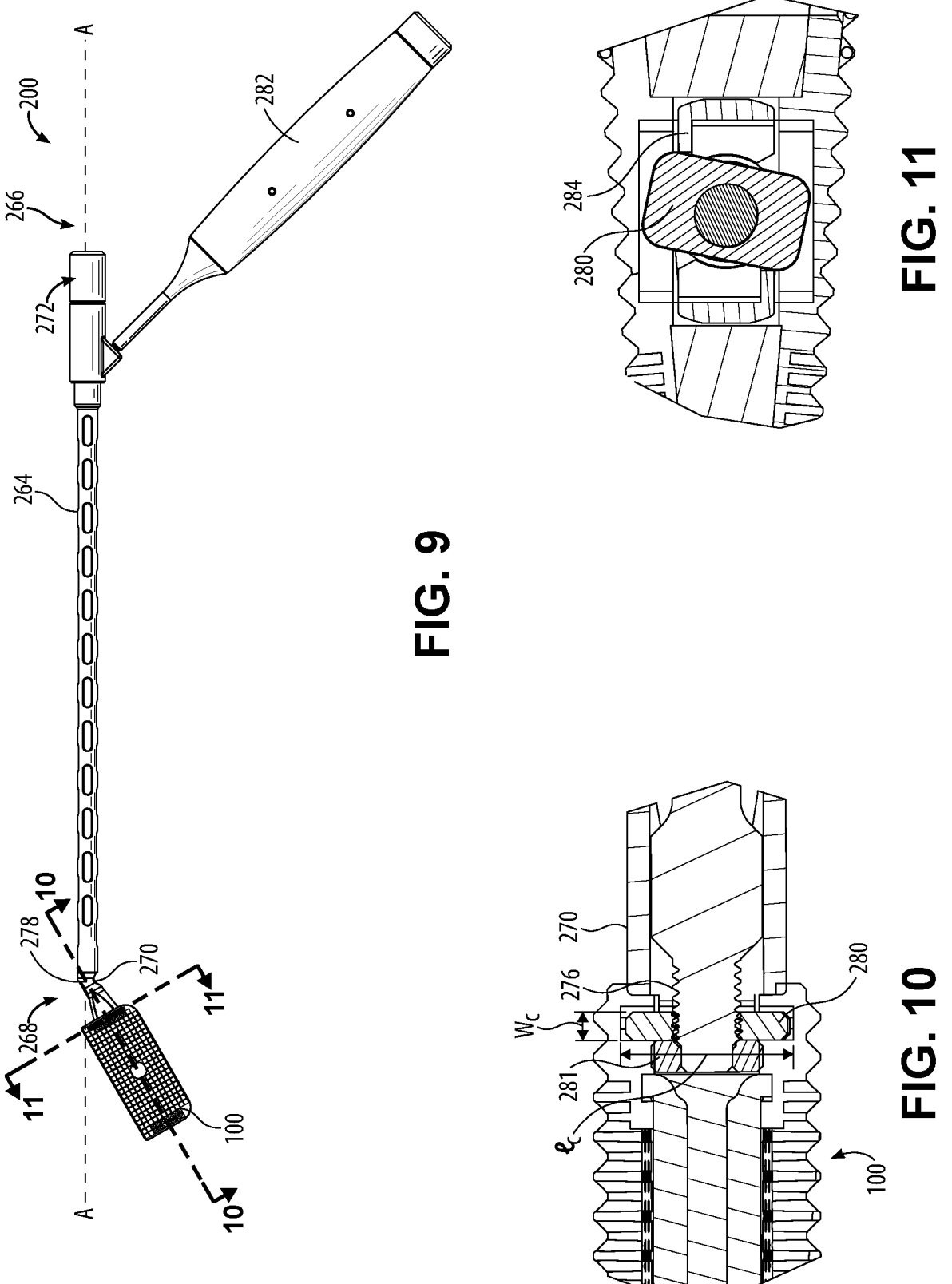
FIG. 9 is a side view of the implant of FIG. 1, showing the implant connected to a tool for implantation.
FIG. 10 is a cross-sectional side view of the tool of FIG. 9, showing the universal joint that allows the angle of the distal end of the tool.
FIGS. 11 and 12 are cross-sectional views looking into the axis and along the axis, respectively, of the connection between the tool and the implant.
Figures 12, 13:
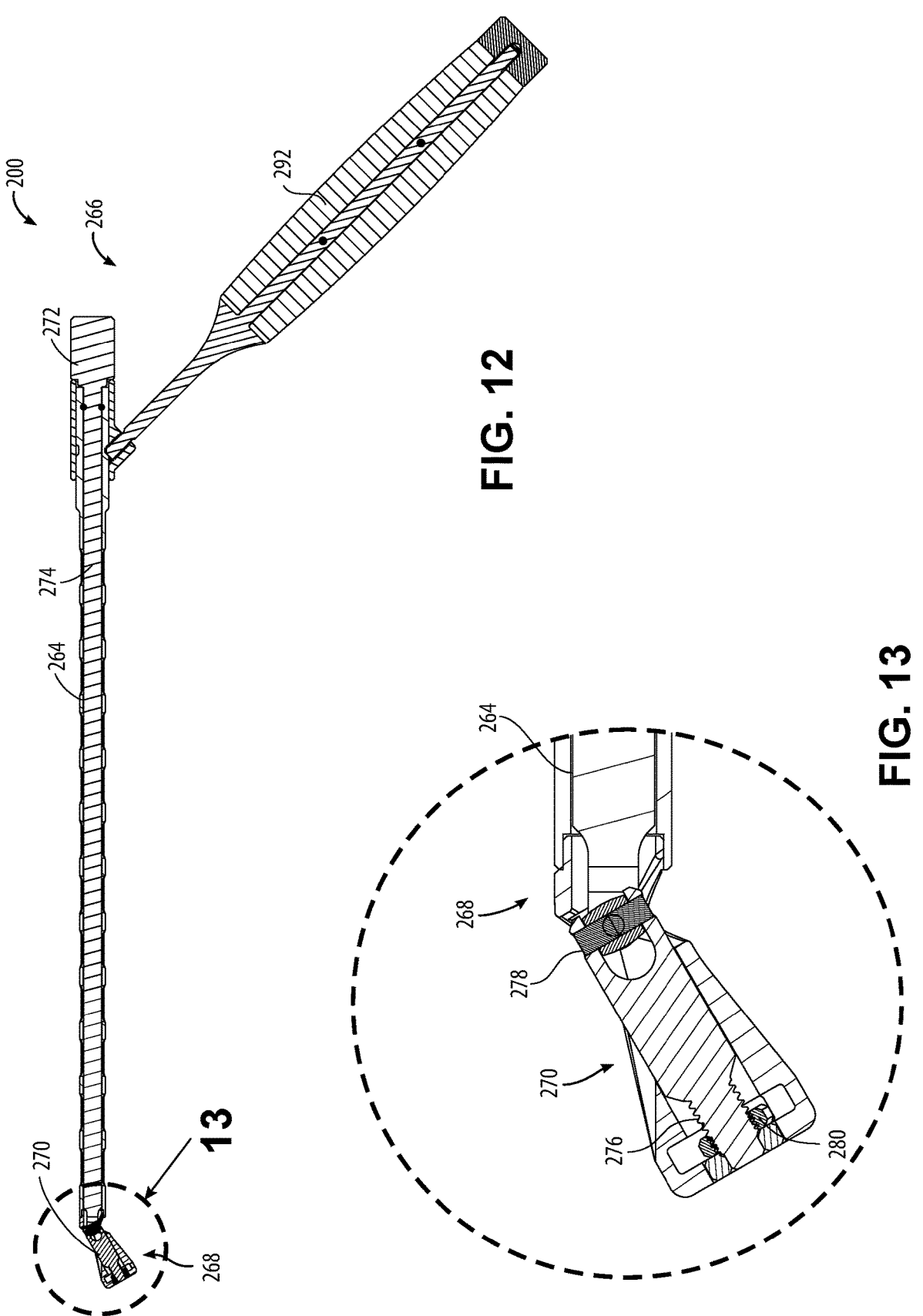
FIG. 13 is a cross-sectional side view of the tool of FIG. 9, showing the locking mechanism for the handle.
Figure 14:
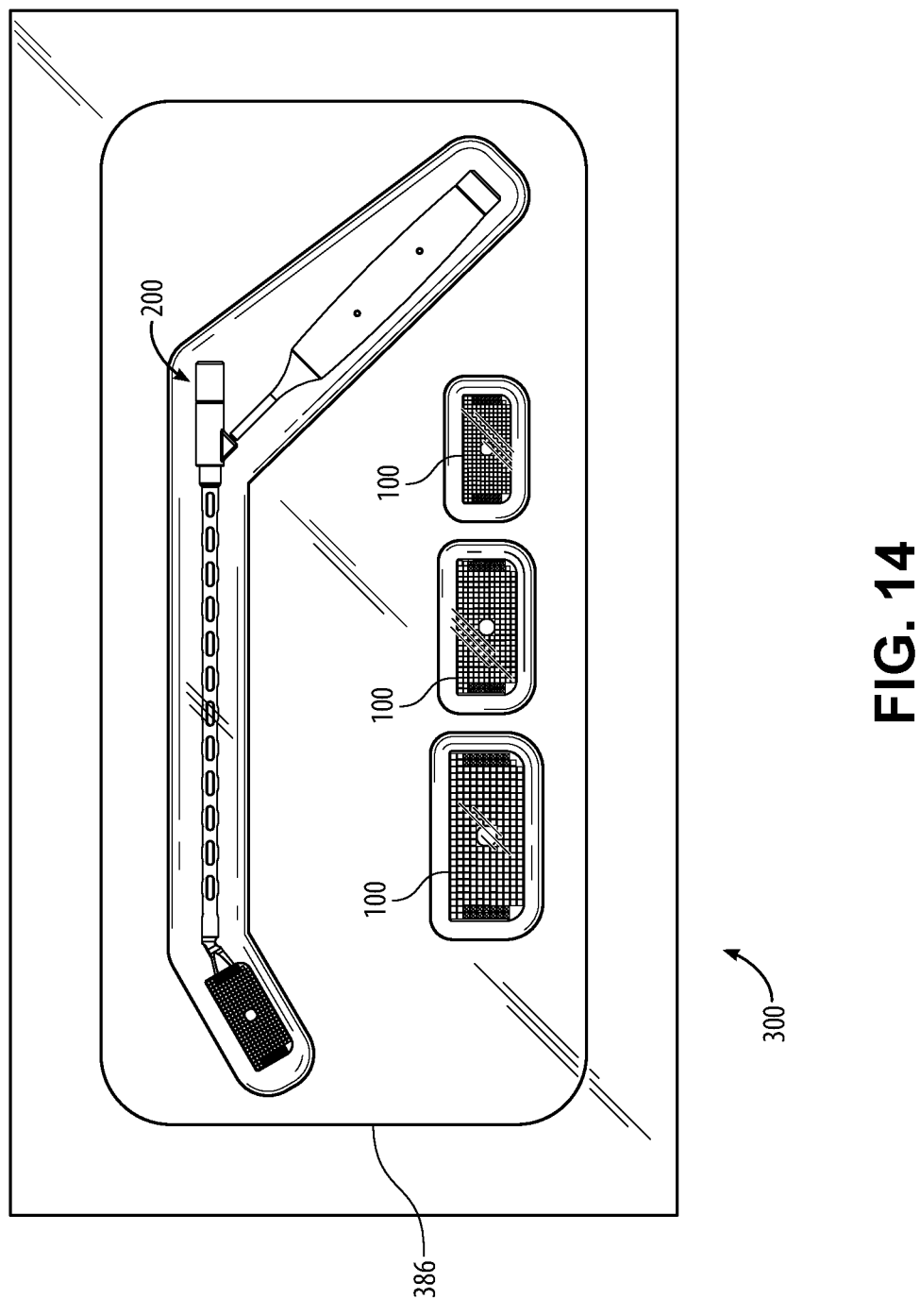
FIG. 14 is a schematic view of a kit including multiple implants of FIG. 1 in a sterile pack.

In embodiments, the inserter head 270 can be angled relative to the main shaft 264, and the set of male threads 276 can connect to the rotation shaft 274 through a universal joint 278 connecting between the main shaft 264 and the inserter head 270 (e.g., as shown in FIG. 10). As shown in FIGS. 11 and 12, a compression plate 280 can be threaded on the set of male threads 270, and the compression plate 280 can have a length lc in a first direction that is greater than a width wc in a second direction perpendicular to the first direction for engaging the recesses 152 in an inserter pocket 150 of the disc replacement implant 100. In embodiments, a bearing 281 can be operatively connected to the distal end of the main shaft 274 for facilitating rotation of the shaft 274 during rotation of the actuating knob 272 and compression plate 280.

A handle 282 can extend obliquely from the proximal portion 266 of the main shaft 264, and the handle 282 can be configured to rotate about a main axis A of the main shaft 264 to reposition the handle 282 relative to the inserter head 270, for example depending on which side of a patient 10 the operation is taking place. Embodiments can include a detent in 284 the main shaft 264 that the handle 282 can lock into to prevent rotation, and can be included on both sides of the main shaft 264 for operating on either side of a patient, e.g., left or right. In embodiments, when the knob 272 is rotated counter clockwise, the compression plate 280 rotates to the left and pulls back (e.g., in the proximal direction towards proximal end 266) and interfaces with the pocket 132, 134 of the implant 100 to retain the implant 100 to the inserter tool 200. Once the implant is placed within the surgical site, to remove the instrument 200 leaving the implant 100 in place, the knob 272 is rotated clockwise to loosen the compression plate 280, placing the compression plate 280 in the position shown in FIG. 11, allowing the inserter 200 to be removed from the implant 100.

In accordance with at least one aspect of this disclosure, a kit 300 for disc replacement can include, a sterile pack 386, a plurality of disc implants 100 as described above of a variety of sizes inside the sterile pack, and optionally a tool 200 as described above.

The methods and systems of the present disclosure, as described above and shown in the drawings, provide for improved access and insertion of the implant during the procedure, as well as improved osseointegration of the implant once implanted in the patient and improved performance of the implant in mimicking a natural disc. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A disc replacement implant comprising:
    a first endplate configured to engage a vertebral endplate of a first vertebra adjacent an intervertebral space;
    a second endplate configured to engage a vertebral endplate of a second vertebra opposite the first end plate in the intervertebral space;
    a core between the first and second endplates, wherein the core includes a first core plate that engages an inner surface of the first endplate and a second core plate that engages an inner surface of the second endplate, wherein a first pocket is defined between the first endplate and the first core plate, wherein there are a plurality of holes through the first end plate from an external surface of the first endplate into the first pocket for osseointegration; and
    an annulus surrounding the core and connecting a perimeter of the first endplate to a perimeter of the second end plate.

2. The implant as recited in claim 1, wherein the first endplate and second end plate are metallic.

3. The implant as recited in claim 1, wherein the core is of a material more flexible than that of the first and second endplates.

4. The implant as recited in claim 3, wherein the core is of a polymer material.

5. The implant as recited in claim 3, wherein the annulus is of a material more flexible than that of the core.

6. The implant as recited in claim 5, wherein the annulus is of viscoelastic material.

7. The implant as recited in claim 1, wherein the core includes:
    a spacer between the first and second core plates, wherein the spacer is connected to each of the first and second core plates and is configured to allow bending and twisting motion of the first and second core plates relative to one another.

8. The implant as recited in claim 7, wherein the spacer includes a spherical section and connects a center portion of the first core plate to a center portion of the second core plate, and has a neutral position that maintains a wedge angle and spacing between the first and second core plates.

9. The implant as recited in claim 7, wherein a second pocket is defined between the second endplate and the second core plate, and wherein there are a plurality of holes through the second endplate from an external surface of the second endplate into the second pocket for osseointegration.

10. The implant as recited in claim 1, further comprising,
    a spacer between the first and second core plates, wherein the spacer is connected to each of the first and second core plates and is configured to allow bending and twisting motion of the first and second core plates relative to one another; and
    wherein the annulus includes a portion that extends inwardly between the first and second core plates to the spacer.

11. The implant as recited in claim 1, wherein the first endplate has an external surface defining a plurality of pyramidal teeth, and wherein the second endplate has an external surface defining a plurality of pyramidal teeth.

12. The implant as recited in claim 11, wherein a plurality of the pyramidal teeth of the first endplate have osseointegration holes defined through each pyramidal face thereof, and wherein a plurality of the pyramidal teeth of the second endplate have osseointegration holes defined through each pyramidal face thereof.

13. The implant as recited in claim 12, wherein the first endplate has a biologics aperture therethrough from the external surface of the first endplate into a pocket, wherein the biologics aperture is larger in diameter than the osseointegration holes, for introduction of osseointegration biologics into the first pocket.

14. The implant as recited in claim 1, wherein an inserter pocket is defined on a first end of the first endplate, second endplate, and annulus, wherein the inserter pocket includes a first recess defined on an inward facing surface of the first end plate, and wherein the inserter pocket includes a second recess defined on an inward facing surface of the second end plate.

15. The implant as recited in claim 14, wherein the inserter pocket is defined on a first lateral end of the first endplate, the second endplate, and the annulus, wherein the first endplate, second end plate, and annulus have a length from the first lateral end to an opposite second lateral end thereof that is greater than a width measured from a front side of the first and second endplates and annulus to a back side thereof to facilitate implantation through a lateral approach.

* * * * *